(12) United States Patent
Kim

(10) Patent No.: US 8,034,382 B2
(45) Date of Patent: Oct. 11, 2011

(54) PREPARATION METHOD FOR BIODEGRADABLE MICRO-PARTICLES CONTAINING DRUGS

(75) Inventor: Cherng-Ju Kim, Little Rock, AR (US)

(73) Assignee: The Board of Trustees of the University of Arkansas, Little Rock, AK (US)

( * ) Notice: Subject to any disclaimer, the term of this patent is extended or adjusted under 35 U.S.C. 154(b) by 571 days.

(21) Appl. No.: 12/221,096

(22) Filed: Jul. 31, 2008

(65) Prior Publication Data

US 2010/0028454 A1     Feb. 4, 2010

(51) Int. Cl.
*A61K 9/14* (2006.01)
*A61K 9/48* (2006.01)
*A61K 9/50* (2006.01)
*A61K 9/64* (2006.01)

(52) U.S. Cl. ........ 424/489; 424/491; 424/451; 424/452; 424/460

(58) Field of Classification Search .................. 424/451, 424/452, 460, 489, 491
See application file for complete search history.

(56) References Cited

U.S. PATENT DOCUMENTS

| | | | |
|---|---|---|---|
| 5,631,021 A | 5/1997 | Okada et al. | |
| 2004/0105878 A1 | 6/2004 | Schwendeman et al. | |
| 2006/0024377 A1 | 2/2006 | Ying et al. | |
| 2007/0009605 A1 | 1/2007 | Igatious | |

FOREIGN PATENT DOCUMENTS

WO    WO 2010014176    2/2010

OTHER PUBLICATIONS

C. J. Kim and Y. N. Nujoma, "Drug Release from Erodible Drug-Polyelectrolyte Complex," Eur. Polym. J., 31, 937 (1995).
Birnbaum, DT and L. Brannon-Peppas, 2004, Microparticle drug delivery systems, pp. 117-135, in Drug Delivery Systems in Cancer Therapy, D.M. Brown editor, Humana Press.
C. J. Kim and P. I. Lee, "Effect of Drug Loading on Swelling-Controlled Drug Release from Hydrophobic Polyelectrolyte Beads," Pharm. Res., 9, 1268 (1992).
C. J. Kim and P. I. Lee, "Hydrophobic Anionic Gel Beads for Swelling-Controlled Drug Delivery," Pharm. Res., 9, 195 (1992).
International Search Report and Written Opinion in PCT/US2009/004273, (2009).

*Primary Examiner* — Mina Haghighatian
(74) *Attorney, Agent, or Firm* — Edwards Angell Palmer & Dodge LLP; Kongsik Kim

(57) ABSTRACT

The disclosure provides a method to form sustained release drug-containing microparticles with a biodegradable polymer. The method involves forming a polymer-drug-organic solvent phase, and dispersing the polymer-drug-organic solvent phase in an aqueous suspension of an inorganic gel, which may be hydroxyapatite. The hydroxyapatite appears to coat the polymer-drug-solvent droplets to prevent them coalescing. The solvent then evaporates with stirring of the dispersion, at which time the droplets solidify to drug-containing microparticles. The inorganic gel allows suitably small microparticles to form without use of an organic emulsifier.

18 Claims, 2 Drawing Sheets

US 8,034,382 B2

PREPARATION METHOD FOR BIODEGRADABLE MICRO-PARTICLES CONTAINING DRUGS

BACKGROUND

A variety of dosage forms have been used for drugs that require long-term administration. To reduce the number of doses that need to be given, and to provide a stable level of the drug in the body, these drugs are preferably given in a sustained-release formulation. One type of sustained-release drug formulation that has been used is biodegradable microspheres containing drug trapped inside the microsphere. One such product is LUPRON Depot, which is biodegradable microspheres containing leutinizing hormone-releasing hormone (leuprolide or LHRH). Leuprolide is used for the treatment of hormone-dependent cancers, particularly prostate cancer, and precocious puberty.

Microparticles are particles with a diameter of approximately 1 to 1000 microns. For injection purposes, microparticles smaller than 125 microns are preferred. Microparticles of this size can be injected with a standard hypodermic needle, instead of surgically implanted. One type of microparticle is composed of a network of a biodegradable polymer that entraps a drug. As the polymer biodegrades in the body, the drug is released. The most commonly used biodegrabable polymers are polylactic acid and a copolymer of lactic acid and glycolic acid.

The most widely used methods to prepare biodegrabable microparticles are phase separation, spray drying, and solvent evaporation. Phase separation, also known as coacervation, uses a decrease of the polymer solubility by the addition of a non-solvent. In a typical procedure, biodegradable polymer is dissolved in an organic solvent (e.g., dichloromethane). Lipophilic drugs are dissolved in the polymer solution. Hydrophilic drugs are dissolved in water and then dispersed in the polymer solution (water in oil (w/o) emulsion) or dispersed as a solid powder. A non-solvent (typically silicon oil) is gradually added. Two phases form: a polymer-rich silicon oil phase and a polymer-depleted liquid organic solvent phase. As the organic solvent is extracted or evaporates, polymer microparticles with entrapped drug solidify in the silicon oil phase. The coacervate (silicon oil) adsorbs to the polymer microparticles.

In spray drying, the biodegradable polymer is dissolved in volatile organic solvent, such as dichloromethane. The drug is dissolved or dispersed in the polymer solution. The solution or dispersion is sprayed in heated air. The solvent evaporates, resulting in the formation of solid microparticles.

Solvent evaporation is the most commonly used method of preparing microparticles. In this method a drug-containing organic polymer solution is emulsified into a dispersion medium that is typically aqueous but may be oil. The methods can be further classified into oil in water (o/w), water in oil in water (w/o/w), and oil in oil (o/o) emulsion methods.

In an o/w method, drug and polymer are dissolved in an organic solvent, such as dichloromethane or a methanol/dichloromethane mixture. The drug-polymer-organic solvent solution is dispersed in an aqueous phase. An emulsifier, typically poly(vinyl alcohol), is included in the aqueous phase to help form small organic solvent droplets in the aqueous phase. The organic solvent evaporates with stirring, and with the evaporation, the droplets solidify into polymer microparticles with entrapped drug.

In a w/o/w double emulsion, an aqueous drug solution is prepared and dispersed into a solution of the polymer in an organic solvent to form a water-in-oil emulsion containing the drug and polymer. The w/o polymer-drug emulsion is then emulsified into an aqueous phase to form a w/o/w emulsion. With stirring, the organic solvent evaporates, allowing the polymer-drug droplets in the emulsion to solidify into microparticles.

In an o/o emulsion method, drug and polymer are dissolved in a water-miscible solvent (e.g., acetonitrile). That solution is emulsified into an oily phase in the presence of an emulsifier such as SPAN 80 to form an oil-in-oil emulsion. The organic solvent is extracted by the oil and microparticles can be harvested by filtration.

Prior art methods of forming biodegradable polymer drug-containing microparticles have some disadvantages. Emulsifier or oil can adhere to the microparticles and contaminate them. Some methods are difficult to scale up.

New methods of forming biodegradable drug-containing microparticles are needed.

SUMMARY

The inventor has found new methods of forming microparticles. In one method, leuprolide is dissolved in methanol and PLGA is dissolved in dichloromethane. The leuprolide and PLGA solutions are mixed to form a drug-polymer-organic solvent solution. The drug-polymer solution is added to a larger aqueous phase containing in-situ-formed hyroxyapatite ($Ca_{10}(PO_4)_6(OH)_2$) gel. The hyroxyapatite gel appears to coat the organic droplets to maintain small droplet size and prevent droplets coalescing. The organic solvent evaporates, just as with a standard oil-in-water emulsion method using an organic emulsifier, leaving behind solidified polymer microparticles with entrapped leuprolide. HCl is then added to the suspension, which dissolves the hydroxyapatite. The microparticles can be recovered by centrifugation or filtration from the otherwise clear solution.

One embodiment of the invention provides a method of preparing drug-containing microparticles comprising: (a) dissolving a biodegradable polymer in organic solvent to form a polymer solution; (b) dissolving or dispersing a drug in the polymer solution to form a polymer-drug-solvent phase; (c) mixing the polymer-drug-solvent phase with an aqueous suspension comprising an inorganic gel to form a dispersion comprising polymer-drug droplets dispersed in the aqueous suspension; (d) evaporating the organic solvent from the dispersion to convert the polymer-drug droplets to drug-containing microparticles; and (e) recovering the drug-containing microparticles from the dispersion.

Preferably the ingorganic gel can be dissolved by acid, and the step of recovering the drug-containing microparticles from the dispersion comprises adding acid to the dispersion to dissolve the inorganic gel.

Other embodiments of the invention provide drug-containing microparticles prepared by the methods described herein.

DETAILED DESCRIPTION

Figure 1:
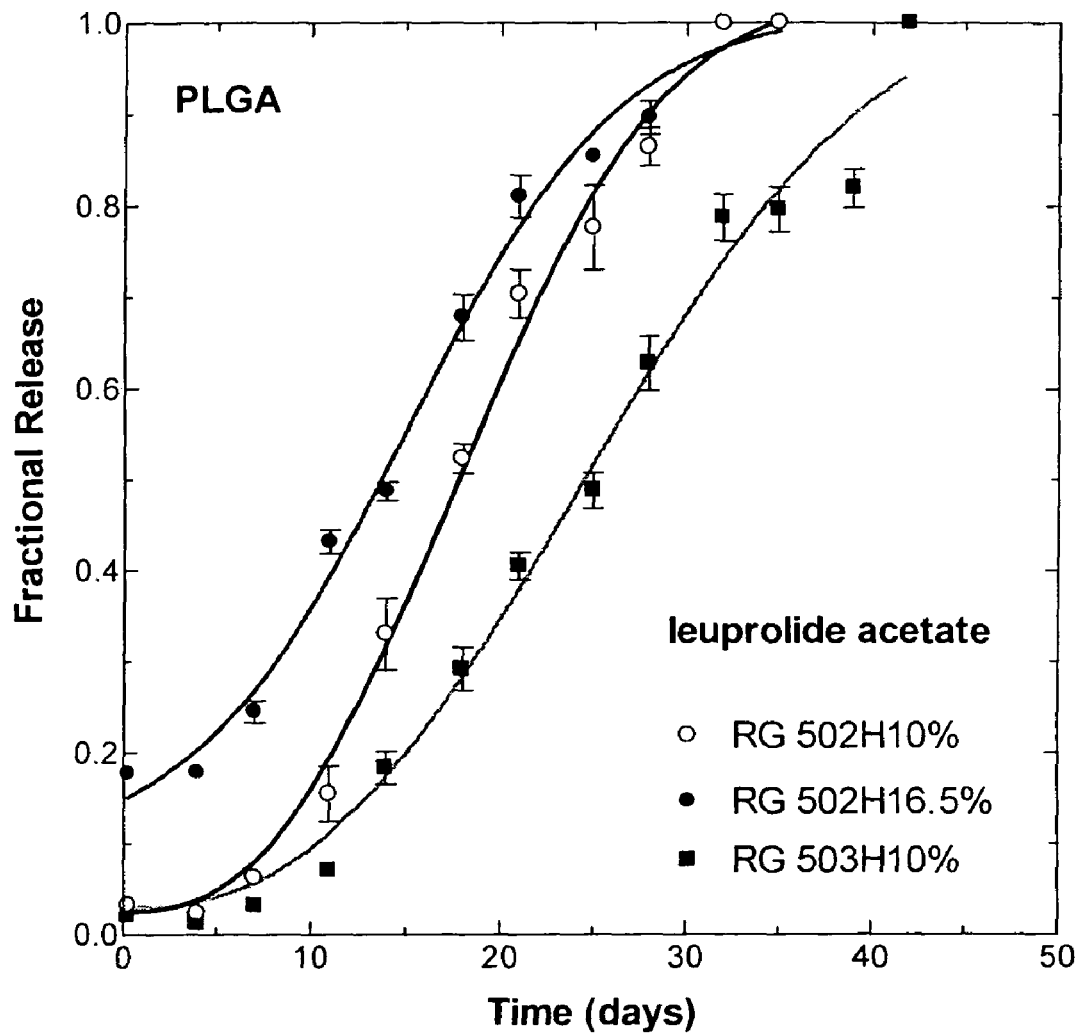
FIG. 1 is a graph of fractional release of leuprolide acetate from PLGA microspheres prepared as described in Example 1 versus time.

This disclosure provides a method of preparing drug-containing microparticles comprising: (a) dissolving a biodegradable polymer in organic solvent to form a polymer solution; (b) dissolving or dispersing a drug in the polymer solution to form a polymer-drug-solvent phase; (c) mixing the polymer-drug-solvent phase with an aqueous suspension comprising an inorganic gel to form a dispersion comprising polymer-drug droplets dispersed in the aqueous suspension; (d) evaporating the organic solvent from the dispersion to convert the polymer-drug droplets to drug-containing microparticles; and (e) recovering the drug-containing microparticles from the dispersion.

This is analagous to an oil-in-water emulsion method for forming microparticles, but without the need for an organic emulsifier. In a traditional evaporation method using an oil-in-water emulsion, a biodegradable polymer is dissolved in organic solvent, and drug is either dissolved in the same solvent in the polymer solution or is dispersed in the polymer solution. The drug may be dissolved in a aqueous solution and the aqueous solution dispersed in the polymer organic solvent solution, or the drug may be dispersed in the form of a dry powder in the polymer solution.

In a conventional oil-in-water emulsion method, the drug-polymer oil phase is dispersed into an aqueous solution with the assistance of a surfactant or emulsifier. The surfactant or emulsifier is necessary to keep droplet size, and thus microparticle size, small.

The inventor has found that hydroxyapatite gel can also protect drug-polymer phase droplets from coalescing, giving consistent and small microparticles. The drug-containing microparticles are produced in good yield, with high encapsulation efficiency of the drug. The particle size is consistent. Since no poly(vinyl alcohol) or other emulsifier needs to be used, the microparticles can be prepared so they are not contaminated with adherent poly(vinyl alcohol). The method uses inexpensive materials and is easily scaled up. The solidified microparticles can be recovered simply by dissolving the hydroxyapatite with acid, and then recovering microparticles by centrifugation or filtration from the clear aqueous solution.

The method can be used to entrap peptide drugs, protein drugs, and small molecule drugs. Both cationic and anionic small molecule drugs have been successfully entrapped in microparticles using the method.

Hydroxyapatite is a preferred inorganic gel for use in the method. But other inorganic gels can also be used.

Preferably the inorganic gel can be dissolved by acid. Preferably the step of recovering the drug-containing microparticles from the dispersion comprises adding acid to the dispersion to dissolve the inorganic gel.

Other apatatites than hydroxyapatite can also be used as the inorganic gel. In particular embodiments, the inorganic gel is fluorapatatite $(Ca_5(PO_4)_3F)$, chlorapatite $(Ca_5(PO_4)_3Cl)$, iodapatite $(Ca_5(PO_4)_3I)$, or carbapatite $(Ca_{10}(PO_4)_6CO_3)$.

$Mg(OH)_2$ and $Al(OH)_3$ have also been tested, and performed well as the inorganic gel. In other specific embodiments, the inorganic gel is dihydroxyaluminum aminoacetate [a basic salt of aluminum and glycine, $(NH_2CH_2COO)Al(OH)_2$] or aluminum phosphate $(AlPO_4)$.

Aluminum phosphate forms by adding phosphoric acid to a solution of aluminum hydroxide. It forms a gel at a lower pH than does hydroxyapatite, specifically at about pH 6 to 7. It also dissolves at a low pH of about pH 1 or 2. Thus, it is suited for encapsulation of anionic drugs at low pHs where carboxyl groups on the drugs are partially or fully protonated.

In specific embodiments, the dispersion does not comprise an organic surfactant or organic emulsifier that assists dispersion of polymer-drug droplets in the aqueous suspension. A surfactant or emulsifier is not necessary because the inorganic gel serves the same function. Furthermore, the inorganic gel completely dissolves with acid, and is easy to separate from the microparticles. In contrast, organic surfactants and emulsifiers are found bound to the microparticles.

Thus, in particular embodiments, the dispersion does not comprise poly(vinyl alcohol).

In some embodiments, an antistatic agent is added to the dispersion before adding acid to dissolve the inorganic gel. Examples of suitable antistatic agents are poly(vinyl alcohol) and poly(vinylpyrolidone-co vinyl acetate). The antistatic agent is added to prevent aggregation of the microparticles. Without the antistatic agent, the microparticles may aggregate and they are often most conveniently recovered by filtration. With the antistatic agent, the microparticles do not aggregate as much, which means the microparticles are smaller. In that case, the microparticles are usually most conveniently recovered by centrifugation. Aggregation does not change the size of the microparticles, and the aggregated microparticles can be disaggregated by physical shear, such as passing through a hypodermic needle in aqueous suspension several times. They can also be disaggregated by resuspending the microparticles in an aqueous solution that contains a surfactant. Typically a Tween 20, Tween 40, or Tween 80 are included in the solution in which microparticles are resuspended for injection. Microparticles are also disaggregated by lyophilization, and typically the harvested microparticles are lyophilized for storage.

Poly(vinyl alcohol) and other polymers can serve either as antistatic agents or as emulsifiers. But an emulsifier is added to the aqueous suspension before adding the polymer-drug-solvent phase in conventional prior art oil-in-water emulsions. It must be present to emulsify the polymer-drug organic solvent droplets before they solidify into microparticles. In contrast, an antistatic agent can be added after the microparticles are formed, immediately before harvesting the microparticles.

Thus, in specific embodiments, the dispersion does not comprise an organic surfactant or organic emulsifier before the drug-containing microparticles are formed (that is, before the polymer-drug droplets solidify into microparticles with evaporation of the organic solvent).

The amount of poly(vinyl alcohol) used as antistatic agent is much less than as an emulsifier. In conventional prior art oil-in-water emulsions, poly(vinyl alcohol) is at a concentration of 0.25%-0.5% (w/v) in the aqueous suspension for use as emulsifier. The inventor has added 0.025 volumes of 0.5% (w/v) poly(vinyl alcohol) solution to the dispersion immediately before adding HCl to dissolve the inorganic gel, where poly(vinyl alcohol) is used as an antistatic agent. Thus, the final concentration of poly(vinyl alcohol) in the dispersion in this case is 0.0125%, much less than when it is used as an emulsifier.

Thus, in specific embodiments, the dispersion comprises no more than 0.05% by weight or no more than 0.02% by weight of organic surfactant, organic emulsifier, or organic antistatic agent.

Two preferred biodegradable polymers for use in the methods of the invention are polylactic acid (PLA) and poly(lactic acid-co-glycolic acid) (PLGA). In other embodiments, the biodegradable polymer is polyglycolic acid. In specific embodiments, the biodegradable polymer is a polyanhydride or a polyorthoester.

The method is effective with both hydrophobic and hydrophilic drugs. Hydrophobic drugs can be codissolved with the polymer in the organic solvent. Hydrophilic drugs may be dissolved first in a more polar organic solvent, such as methanol, and then mixed with the polymer dissolved in a less polar solvent, such as dichloromethane. Alternatively, hydrophilic drugs can be dissolved in an aqueous solution, and the aqueous drug solution can be dispersed into an organic solvent solution containing the polymer. This forms a water-in-oil dispersion for the drug-polymer phase. Hydrophilic drugs may also be directly dispersed as a solid powder in a polymer solution in an organic solvent.

Any suitable organic solvent can be used for the polymer-drug phase. These include dichloromethane, ethyl acetate, acetonitrile, and methanol, and mixtures thereof. The organic solvent should at least include an organic solvent that is immiscible with water, such as dichloromethane or ethyl acetate. Water-miscible solvents such as methanol or acetonitrile can be mixed with the water-immiscible solvent. A water-miscible solvent may be used to assist in dissolving hydrophilic drugs to get the drug into the oil phase in the dispersion.

The inventor has found that the best encapsulation efficiency and microparticle yield with basic amine-containing drugs, including leuprolide and verapamil HCl, nicardipine HCl, was achieved at a pH of about 9.0 to 10.0. Above pH 10, the PLA and PLGA polymers begin to hydrolyze and solubilize. This decreases the microparticle yield. The basic drugs are in a less ionized state at pH 9 to 10 than they are at lower pHs, and this is believed to cause them to stay associated with the polymers better. But even at pH 7.0, the encapsulation efficiency for leuprolide was 90%. So a variety of pHs of the aqueous suspension may be used.

With acidic carboxyl-containing drugs, including piroxicam, naproxen acid, and salicylic acid the inventor has found that the best encapsulation efficiency is obtained at about pH 5.0. It is believed that this is because at more acidic pHs the acid drugs are less ionized, and in the nonionized state they associate with the polymers better and do not tend to partition into the aqueous phase as much.

Below about pH 5, hydroxyapatite crystallizes and in the crystal form it loses the ability to prevent coalescence of the drug-polymer phase droplets. Thus, with hydroxyapatite at least, the aqueous suspension is preferably at a pH of about 5 or above.

In the Example below, 2 or 3 ml of drug-polymer solution containing 20% PLGA and 10% leuprolide acetate was mixed with 400 ml of aqueous suspension containing hydroxyapatite prepared with 6 g of CaO. Higher amounts of drug-polymer solution can be mixed with the inorganic gel aqueous suspension, but higher concentrations of inorganic gel must also be used. The inventor has used as much as 100 ml of drug-polymer solution mixed with 400 ml of aqueous suspension containing higher amounts of hydroxyapatite.

In mixing the drug-polymer phase with the aqueous suspension, a high mixing rate is used initially to form small droplets. In the Example below 5,000 rpm or higher was used for 5 minutes. After this short period of rapid mixing to form a dispersion with small drug-polymer droplets, the stirring rate is decreased to, e.g., 600 rpm. Stirring is continued for a longer period of time, typically one hour or longer, to allow evaporation of the organic solvent. During this time, solidified microparticles form as the solvent evaporates.

The microparticle size can be varied by methods known in the art. A higher stirring rate during the mixing phase of mixing the drug-polymer phase with the aqueous suspension produces smaller droplets and thus smaller microparticles. A lower polymer concentration in the drug-polymer phase produces smaller particles because the lower polymer concentration produces a less viscous solution that tends to form smaller droplets. Longer polymers will produce a more viscous solution than shorter polymers at the same concentration, and thus longer polymers will tend to produce larger microparticles. The organic solvent also affects microparticle size. If the polymer is highly soluble in the solvent, the drug-polymer phase will be less viscous and smaller microparticles will be formed. If the polymer is less soluble in the organic solvent, larger microparticles will be formed.

Any suitable drug can be formulated into these drug-containing microparticles. In one embodiment, the drug is a protein. In another embodiment, the drug is a peptide (e.g., a peptide of 2 to 50 amino acids in length). In another embodiment, the drug is a small molecule, e.g., a molecule with a molecular weight of less than 1000 or less than 500. In some embodiments, the small molecule is non-peptidyl.

In one embodiment, the drug is a peptide analog of leutenizing hormone-releasing hormone (LHRH). Examples of suitable LHRH peptide analogs are leuprolide, triptorelin, and goserelin, and pharmaceutically acceptable salts thereof.

In specific embodiments, the drug is risperidone, octreotide, somatostatin, human growth hormone, deslorelin, buserelin, felypressin, gondorelin, oxytocin, vasopressin, fertirelin, histrelin, nafarelin, sincalide, thymopentin acetate, naltrexone, or a pharmaceutically acceptable salt thereof.

In other embodiments, the drug is verapamil, nicardipine, piroxicam, naproxen acid, salicylic acid, or a pharmaceutically acceptable salt thereof.

EXAMPLE

Materials and Methods

Leuprolide acetate and poly(lactic acid-co-glycolic acid) (PLGA) RG502H or PLA R202H were dissolved in a 24/76 (v/v) methanol/dichloromethane mixture at a concentration of 20% polymer and 10% leuprolide (w/v) to prepare the polymer-drug solution. An aqueous suspension of hyroxyapatite was prepared by dissolving 6 g of CaO in 400 ml water. Then phosphoric acid was added to adjust the pH of the aqueous suspension to between 9.0 and 10.0. Hydroxyapatite gel was formed in situ in the aqueous suspension under these conditions by the reaction $10\ CaO + 6\ H_3PO_4 = Ca_{10}(PO_4)_6(OH)_2 + 8\ H_2O$. The drug/polymer solution (2 or 3 ml) was dispersed into the aqueous suspension medium. The dispersion was initially homogenized by a high-shear mixer at 5,000 or more rpm for 5 minutes. The solvents were then evaporated by stirring at 600 rpm for 1 hour or longer. Then concentrated HCl was added slowly until the hydroxyapatite dissolved and the suspension cleared. Hydroxyapatite is dissolved by the reaction $Ca_{10}(PO_4)_6(OH)_2 + 20\ HCl = 10\ CaCl_2 + 6\ H_3PO_4 + 2\ H_2O$. The solidified microparticles were recovered by centrifugation and filtration.

Results and Discussion:

PLA and PLGA microparticles were examined and photographed microscopically (data not shown). Most of the microparticles were found to be in the size range of 10-20 microns, which is a size suitable for injection.

Encapsulation efficiency of leuprolide acetate was 95% or higher when the pH of the suspending medium was pH 9.0 to pH 10.0. Encapsulation efficiency refers to the mass of drug recovered in microparticles divided by the starting mass of drug in the polymer-drug phase. To quantify drug in microparticles, the microparticles were first dissolved in an ethanol/dichloroethane (28/72 v/v) mixture. The drug content of the solution was then measured by ultraviolet absorption.

In other experiments, the pH of the suspending medium was varied. The encapsulation efficiency of leuprolide acetate decreased to 90% at pH 7.0, and decreased further at lower pHs. Small anionic and cationic small molecule drugs were also tested. Encapsulation of amine-containing cationic drugs was highest at approximately pH 9.0 to 10.0. It is believed that this is because the amine groups are largely unprotonated at elevated pH. At lower pHs where the drug amine groups are protonated, the drugs are more water soluble and thus partition more away from the polymer-drug droplets. With anionic drugs containing carboxyl groups, the pH relationship is reversed. The carboxyl groups are non-ionized at lower pHs, and therefore these drugs are less water-soluble at lower pHs. Thus, the anionic drugs have been found to have better encapsulation efficiency at lower pHs, e.g., about pH 5.0. Verapamil HCl and nicardipine HCl were the small-molecule amine-containing drugs tested. Piroxicam, lidocaine, and salicylic acid were the small molecule anionic drugs tested.

Above pH 10 PLA and PLGA polymers are hydrolyzed to an extent, and this decreases the yield of microparticles. Yield is defined herein as the recovered mass of microparticles divided by the starting mass of (polymer plus drug). At pHs below about 5, hydroxyapatite crystallizes, instead of forming a gel. Without the hydroxyapatite gel, the polymer-drug droplets coalesce and the solid particles formed are too large.

The release kinetics of leuprolide acetate from the PLGA microparticles prepared as described herein was determined and the results are shown in FIG. 1. Concentration of drug in the supernatant was measured by ultraviolet absorption. The release of leuprolide acetate from PLGA microparticles shows a typical tri-phase. Initial burst release occurs due to the fast dissolution of peptide located at the microparticle surface followed by a time lag of 4-5 days. After 4-5 days the microparticles have hydrated significantly and then erode due to the breakdown of the polymer. During the middle portion of the curve, peptide release occurs at a near constant rate.

Figure 2:
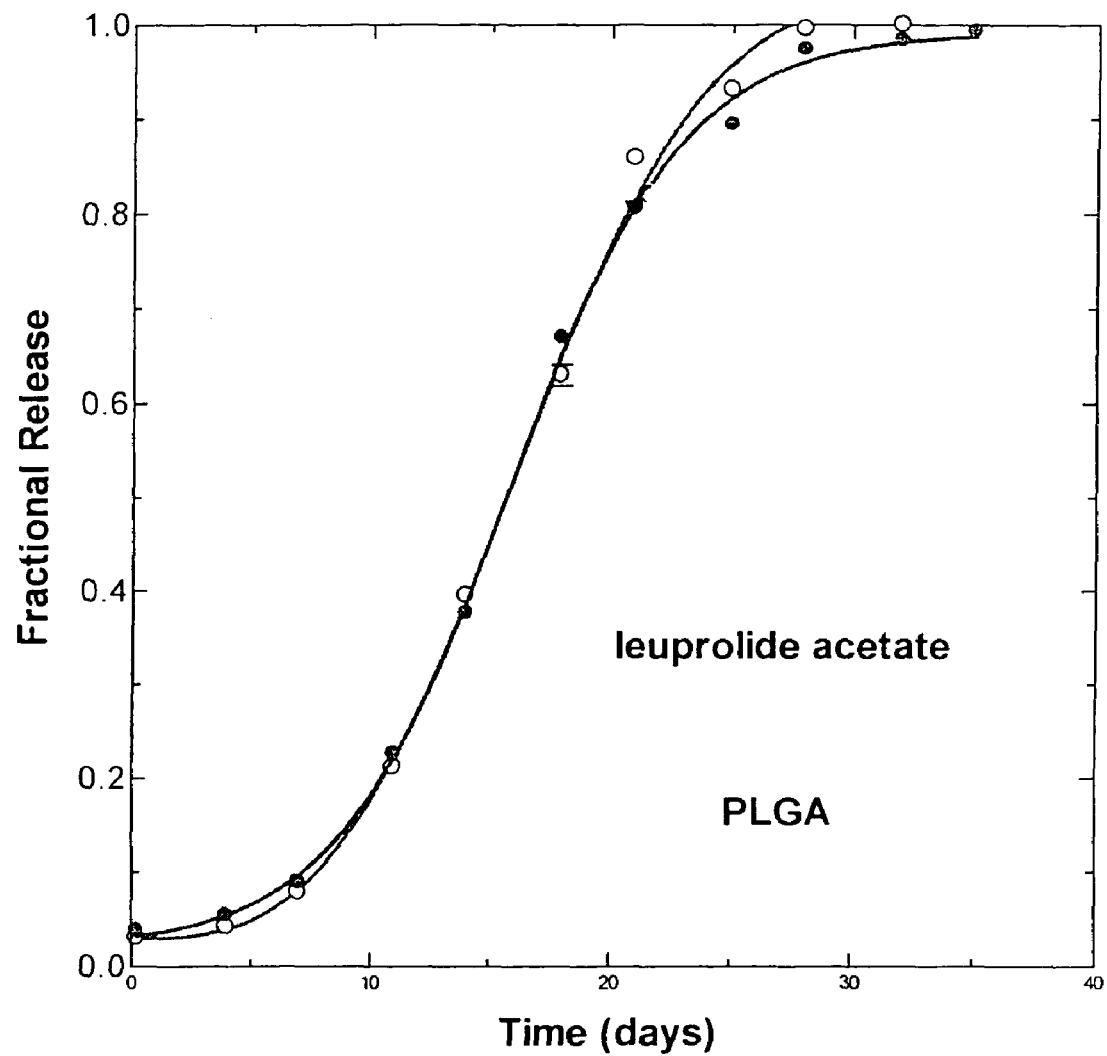
FIG. 2 is a graph showing a comparison of the kinetic profile of drug release of leuprolide acetate from FIG. 1 using 10% PLGA microspheres as prepared in Example 1 (○), and for comparison the published time release profile of leuprolide acetate from conventionally prepared microspheres (●) (D'Souza S S et al., *AAPS PHARM Sci. Tech.* 6(4), E553-564, 2005).

FIG. 2 compares the release curve of FIG. 1 for 10% RG 502H with a published release curve for leuprolide acetate from microparticles formed by conventional oil-in-water emulsion with poly(vinyl alcohol) as emulsifier (D'Souza et al., 2005, *AAPS PHARM. Sci. Tech.* 6(4), E553). The release curves are nearly identical.

All patents, patent documents, and other publications cited are hereby incorporated by reference.

What is claimed is:

1. A method of preparing drug-containing microparticles comprising:
   dissolving a biodegradable polymer in organic solvent to form a polymer solution;
   dissolving or dispersing a drug in the polymer solution to form a polymer-drug-solvent phase;
   mixing the polymer-drug-solvent phase with an aqueous suspension comprising an inorganic gel to form a dispersion comprising polymer-drug droplets dispersed in the aqueous suspension, wherein the inorganic gel can be dissolved by acid, and the dispersion is essentially free of organic surfactants and organic emulsifiers;
   evaporating the organic solvent from the dispersion to convert the polymer-drug droplets to drug-containing microparticles; and
   recovering the drug-containing microparticles from the dispersion, wherein the step of recovering the drug-containing microparticles from the dispersion comprises adding acid to the dispersion to dissolve the inorganic gel.

2. The method of claim 1 wherein the organic solvent is a mixture of organic solvents.

3. The method of claim 2 wherein the organic solvent comprises methanol and dichloromethane.

4. The method of claim 1 wherein the drug is hydrophobic.

5. The method of claim 1 wherein the drug is hydrophilic.

6. The method of claim 1 wherein the drug is a peptide or polypeptide.

7. The method of claim 6 wherein the drug is leuprolide.

8. The method of claim 5 wherein the drug is dissolved in an aqueous solution to form a drug-containing aqueous solution, and the drug-containing aqueous solution is dispersed in the polymer solution to form the polymer-drug-solvent phase.

9. The method of claim 1 wherein the inorganic gel is an apatite.

10. The method of claim 9 wherein the apatite is hydroxyapatite.

11. The method of claim 9 wherein the apatite is carbapatite, fluorapatite, or chlorapatite.

12. The method of claim 1 wherein the inorganic gel is dihyroxyaluminum aminoacetate, $Al(OH)_3$, $AlPO_4$, or $Mg(OH)_3$.

13. The method of claim 1 wherein the dispersion does not comprise poly(vinyl alcohol).

14. The method of claim 1 wherein the dispersion comprises an organic antistatic agent, and said organic antistatic agent is present in no more than 0.05% (w/w) of the dispersion.

15. The method of claim 1 wherein the biodegradable polymer is polylactic acid or polyglycolic acid or polylactic acid-co-glycolic acid).

16. The method of claim 1, wherein said drug is an amine-containing drug, and said method further comprises adjusting the pH value of said aqueous suspension comprising an inorganic gel to about 9.0 to 10.0.

17. The method of claim 1, wherein said drug is an acidic carboxyl-containing drug or an anionic drug, and said method further comprises adjusting the pH value of said aqueous suspension comprising an inorganic gel to about 5.0.

18. A method of preparing microparticles containing a hydrophilic drug, said method comprising:
   dissolving a biodegradable polymer in organic solvent to form a polymer solution;
   dispersing said drug as a solid powder into the polymer solution to form a polymer-drug-solvent phase;
   mixing the polymer-drug-solvent phase with an aqueous suspension comprising an inorganic gel to form a dispersion comprising polymer-drug droplets dispersed in the aqueous suspension, wherein the inorganic gel can be dissolved by acid, and the dispersion is essentially free of organic surfactants and organic emulsifiers;
   evaporating the organic solvent from the dispersion to convert the polymer-drug droplets to drug-containing microparticles; and
   recovering the drug-containing microparticles from the dispersion, wherein the step of recovering the drug-containing microparticles from the dispersion comprises adding acid to the dispersion to dissolve the inorganic gel.

* * * * *